United States Patent

Olson et al.

[11] Patent Number: 5,817,151
[45] Date of Patent: Oct. 6, 1998

[54] CIRCUIT DETECTABLE PACKAGED MEDICAL ELECTRODES

[75] Inventors: Kenneth F. Olson, Edina; John F. Stolte, Burnsville; Nora J. Utke, Minneapolis; Gary B. Stendahl, Crystal, all of Minn.

[73] Assignee: SurVivaLink Corporation, Minnetonka, Minn.

[21] Appl. No.: 658,200

[22] Filed: Jun. 4, 1996

[51] Int. Cl.[6] .................................................. A61N 1/04
[52] U.S. Cl. ........................ 607/142; 607/152; 206/438
[58] Field of Search ............................. 607/5, 115, 142, 607/148, 152; 128/639; 206/363, 438

[56] References Cited

U.S. PATENT DOCUMENTS

| | | | |
|---|---|---|---|
| 3,685,645 | 8/1972 | Kawaguchi | 206/438 |
| 4,423,732 | 1/1984 | Tarjan et al. | 206/438 |
| 4,494,552 | 1/1985 | Heath . | |
| 4,543,958 | 10/1985 | Cartmell | 607/152 |
| 4,777,954 | 10/1988 | Keusch et al. | 607/152 |
| 5,255,677 | 10/1993 | Schaefer et al. | 607/152 |
| 5,354,321 | 10/1994 | Berger | 607/152 |
| 5,366,497 | 11/1994 | Ilvento et al. | 607/142 |
| 5,402,884 | 4/1995 | Gilman et al. . | |
| 5,462,157 | 10/1995 | Freeman et al. | 206/438 |
| 5,466,217 | 11/1995 | Myers et al. | 607/152 |
| 5,562,710 | 10/1996 | Olsen et al. . | |

FOREIGN PATENT DOCUMENTS

WO 94/26350  11/1994  WIPO .

*Primary Examiner*—Marvin M. Lateef
*Assistant Examiner*—George R. Evanisko
*Attorney, Agent, or Firm*—Patterson & Keough, P.A.

[57] ABSTRACT

A circuit detectable arrangement of electrodes and a package thereof are provided so that the presence of a fresh package of electrodes can be detected by a device and can be distinguished from electrodes that have been used or tampered with. A first electrode is disposed on an electrically non-conductive liner, a second electrode is disposed on an electrically non-conductive liner, and an electrical connector is provided between the first and second electrodes for electrically completing a circuit connecting the lead wire of the first electrode to the lead wire of the second electrode. An electrode package is also provided including the first and second electrodes therein. Within the package, the first and second electrodes are provided adjacent to one another with their backing layers generally parallel to one another and with a loop formed in the electrical connector. The loop extends across the tear line and into the interior portion of the package so that by opening the package along the tear line, the electrical connector can be broken. The electrical connector may also include a strip of tear resistant material which is positioned within the interior portion of the package. Opening of the package can be facilitated by extending the strip of tear resistant material or a portion of the electrical connector through an opening of the package to provide a gripping means. Alternatively, at least one of the lead wires can be threaded within the package through the loop and within the interior portion so as to pass through the material of the package from said interior portion and provide an easy opening feature.

28 Claims, 6 Drawing Sheets

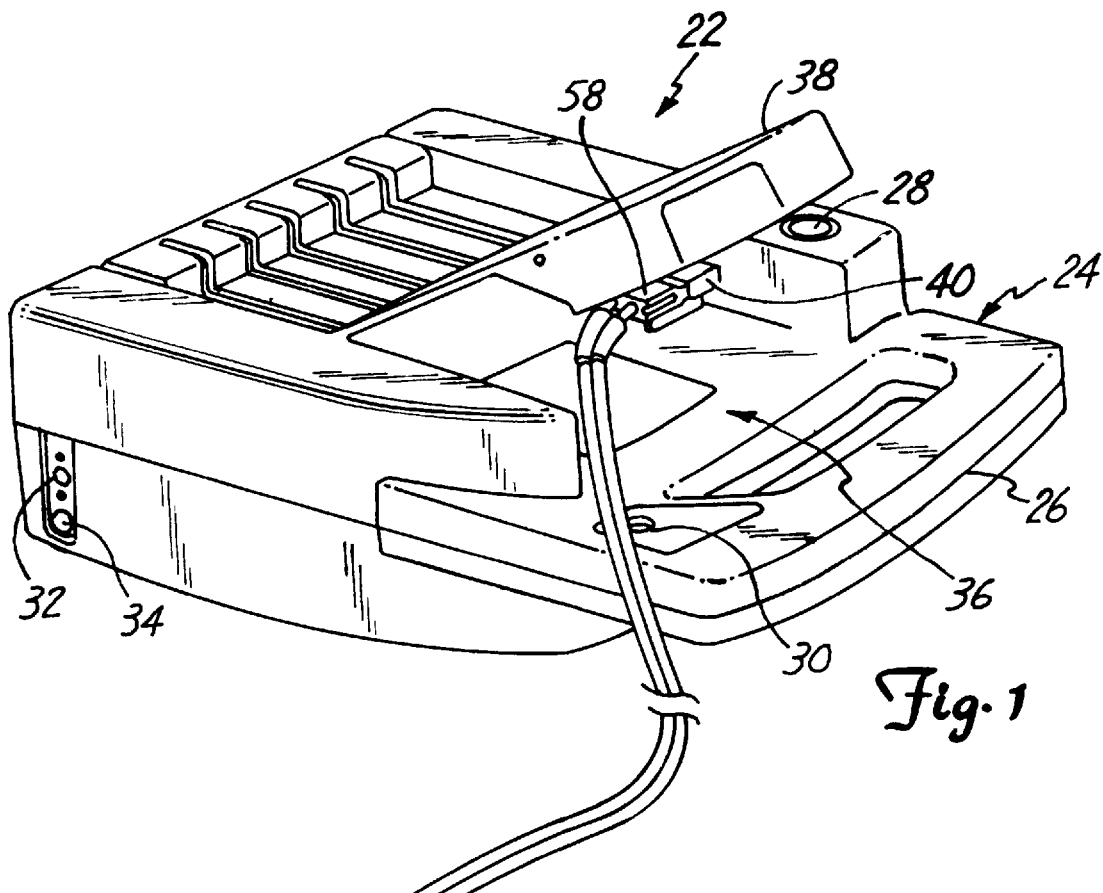
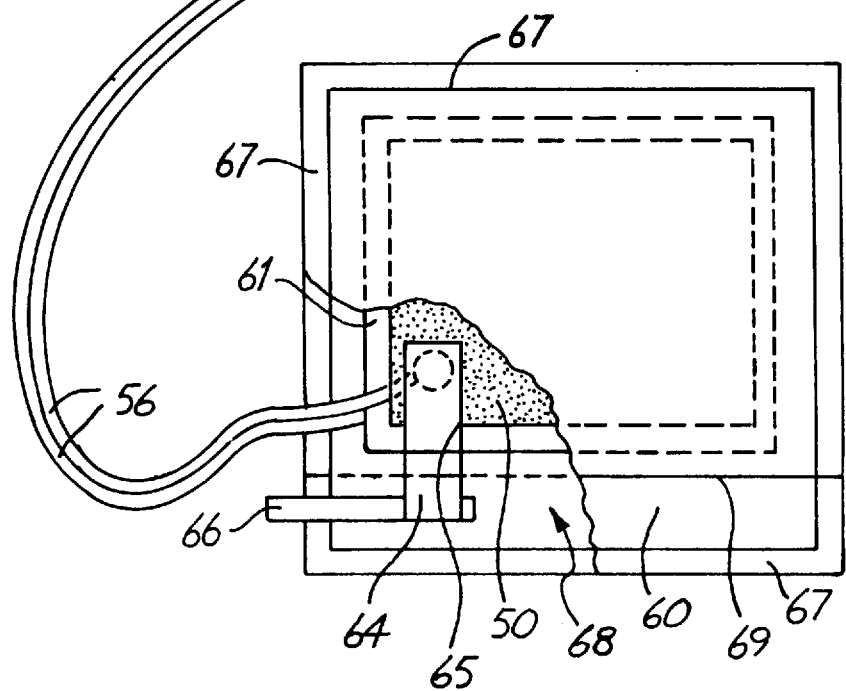
Fig. 1

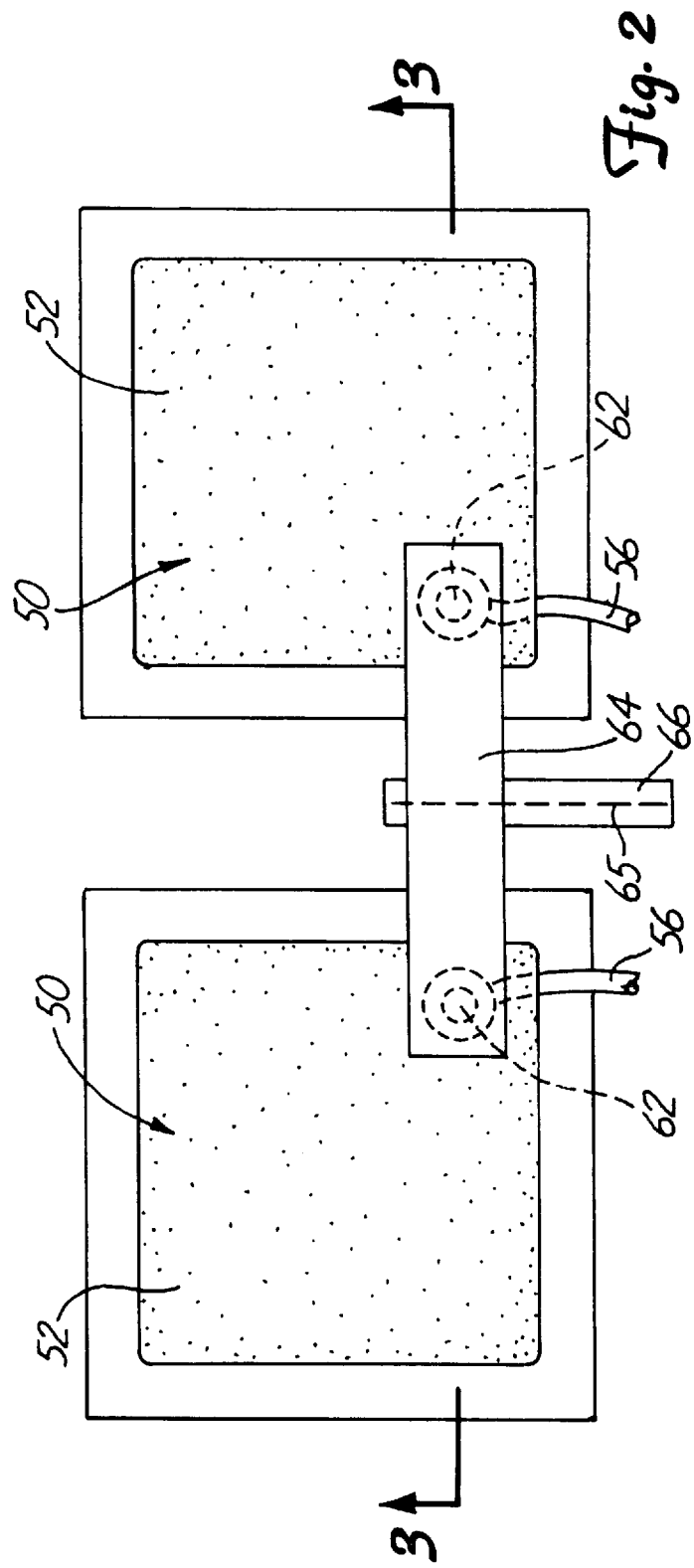

CIRCUIT DETECTABLE PACKAGED MEDICAL ELECTRODES

RELATED APPLICATIONS

The present invention is related to co-pending U.S. patent application Ser. No. 08/512,441, entitled Automated External Defibrillator with Self-Test System and co-pending U.S. patent application Ser. No. 08/644,227, entitled Defibrillator Electrodes and Date Code Detector Circuit filed May 10, 1996, and U.S. patent application Ser. No. 08/411,102, entitled Medical Electrode Packaging Technology. Each of the above Applications are assigned to the assignee of the present invention and each are herein incorporated by reference.

FIELD OF THE INVENTION

The present invention relates to packaged disposable electrodes. In particular, the present invention is an arrangement of medical electrodes and the package thereof which when in the package and connected with an external device completes a detection circuit.

BACKGROUND OF THE INVENTION

Electrodes are used with numerous devices in the medical field. One such application is with an automated external defibrillator (AED). AEDs are used by first-responder emergency medical technicians to resuscitate cardiac arrest patients. It is important that AEDs carried by these technicians be continuously operational and ready for use on a moment's notice. To help ensure a high level of confidence that they will be operational when needed, AEDs must be periodically checked and tested by the technicians, and corrective maintenance performed if any faults are identified. AED's functions and components that should be periodically checked and tested, for example, include the charge state of batteries, the presence of electrodes and the ability of the device to charge and deliver defibrillation pulses.

An automated external defibrillator with self-test system has been developed and is disclosed in co-pending U.S. patent application Ser. No 08/512,441, entitled Automated External Defibrillator with Self-Test System, which is commonly assigned to the assignee of the subject application, and the entire contents of which are incorporated herein by reference. Disclosed is a defibrillator that includes a digital control system having self-test means for periodically and automatically performing self-tests of one or more defibrillator components. If a malfunctioning component is identified, the self-test means actuates an audible alarm or other maintenance indicator to alert an operator. Specifically tested functions include the presence and inter-connection of defibrillator electrodes, battery-charge state, the functionality of the high voltage circuit and the functionality of the digital control system. Some functions are self-tested daily, while others are self-tested weekly.

In order to test the presence and interconnection of defibrillator electrodes, the defibrillator electrodes must be packaged or otherwise arranged in a way to permit the testing. Specifically, it is described in the aforementioned co-pending application Ser. No. 08/512,441 that a pair of electrodes together form a part of an electric circuit through which current is run during the self-test and the impedance measured. A relatively low impedance, (e.g., less than about 10 ohms) indicates the presence of a pair of electrodes. In order for the electrodes to make up and complete an electrical circuit, both electrodes are electrically connected with one another so that a circuit can comprise the electrical lead wires of each electrode. To do this, the electrically conducive adhesive layers of each of the pair of electrodes are affixed in a face-to-face orientation to opposite sides of a release liner within a package. The release liner is perforated with a number of apertures so that the electrodes are electrically coupled to one another within the package. A relatively low resistance electrical circuit is thereby established between the ends of the lead wires.

The above-described system effectively detects the presence of a pair of electrodes as provided in the package. An additional advantage is that the freshness of the packaged electrodes can be determined because the conductive adhesive layers increase in resistance as they dry out over time. However, a problem that the circuit cannot distinguish between is new electrodes and electrodes that have been used or tampered with and subsequently stuck back together, with or without the perforated release liner.

Medical electrode packaging is also described in U.S. Pat. No. 5,402,884 to Gilman, et al., which is assigned to the assignee of the present invention. In one embodiment, a sealed package is disclosed containing a pair of medical electrodes with conductive adhesive layers facing one another and separated from one another by a resistive layer. A circuit can be completed through the lead wires of each electrode, through the conductive adhesive of each electrode, and through the resistive layer. Again, by monitoring resistance through the circuit, the presence of the electrodes can be detected. Also disclosed in the Gilman, et al. patent are a number of other packages for single medical electrodes. In each case, at least one conductor is provided through the package so that a circuit can be completed through the package and a portion of the conductive adhesive layer of the one electrode. While these packages are useful for their intended purpose, they require special components for construction and for monitoring.

SUMMARY OF THE INVENTION

In accordance with the present invention, a circuit detectable arrangement of medical electrodes and a package thereof are provided that overcome the disadvantages and shortcomings of the prior art. Specifically, by the arrangement of the electrodes and the package design of the present invention, the presence of a fresh package of electrodes can be detected and distinguished from electrodes that have been used or tampered with. In other words, by the present invention, a fresh and non-opened package of electrodes can be detected.

In accordance with one aspect of the present invention, a circuit detectable arrangement of a plurality of medical electrodes is provided with each electrode having an electrically non-conductive backing layer, a layer of electrically conductive adhesive disposed on the backing layer and a lead wire extending therefrom and electrically connected with the conductive adhesive. More specifically, a first electrode is disposed on an electrically non-conductive liner, a second electrode is disposed on an electrically non-conductive liner, and an electrical connector is provided between the first and second electrodes for electrically completing a circuit connecting the lead wire of the first electrode to the lead wire of the second electrode. Preferably, the backing layers of the first and second electrodes each include a conductor portion, and the electrical connector is connected between the conductor portion of the backing layer of the first electrode and the conductor portion of the backing layer of the second electrode. The electrical connector preferably comprises a strip of flexible and electrically conductive material and may include a non-conductive tear resistant strip.

In accordance with another aspect of the present invention, an electrode package is provided which is made of flexible material defining a pouch and having an interior cavity including first and second medical electrodes within an electrode receiving space therein. Moreover, in accordance with a package construction of the present invention, the lead wires from the first and second electrodes extend through an opening provided through the package to the outside of the package, and the package has a tear line along which the package is to be opened and which divides the interior cavity of the package into an electrode receiving space and an interior portion. Within the package, the first and second electrodes are provided adjacent to one another with their backing layers generally parallel to one another and with a loop formed in the electrical connector. The loop extends across the tear line and into the interior portion of the package so that by opening the package along the tear line, the electrical connector can be broken. The electrical connector may also include a strip of tear resistant material which is positioned within the interior portion of the package. Opening of the package can be facilitated by extending the strip of tear resistant material or a portion of the electrical connector through an opening of the package to provide a gripping means. Alternatively, at least one of the lead wires can be threaded within the package through the loop and within the interior portion so as to pass through the material of the package from the interior portion and provide an easy opening feature.

BRIEF DESCRIPTION OF THE DRAWINGS

FIG. 1 is a perspective view of an automated external defibrillator (AED) with a pair of electrodes according to the present invention attached thereto.

FIG. 2 is a detailed plan view of unpackaged electrodes positioned on release liners.

FIG. 3 is a cross-sectional view through the pair of electrodes of FIG. 2 taken along line 3—3.

DETAILED DESCRIPTION OF THE PREFERRED EMBODIMENTS

Figure 4:
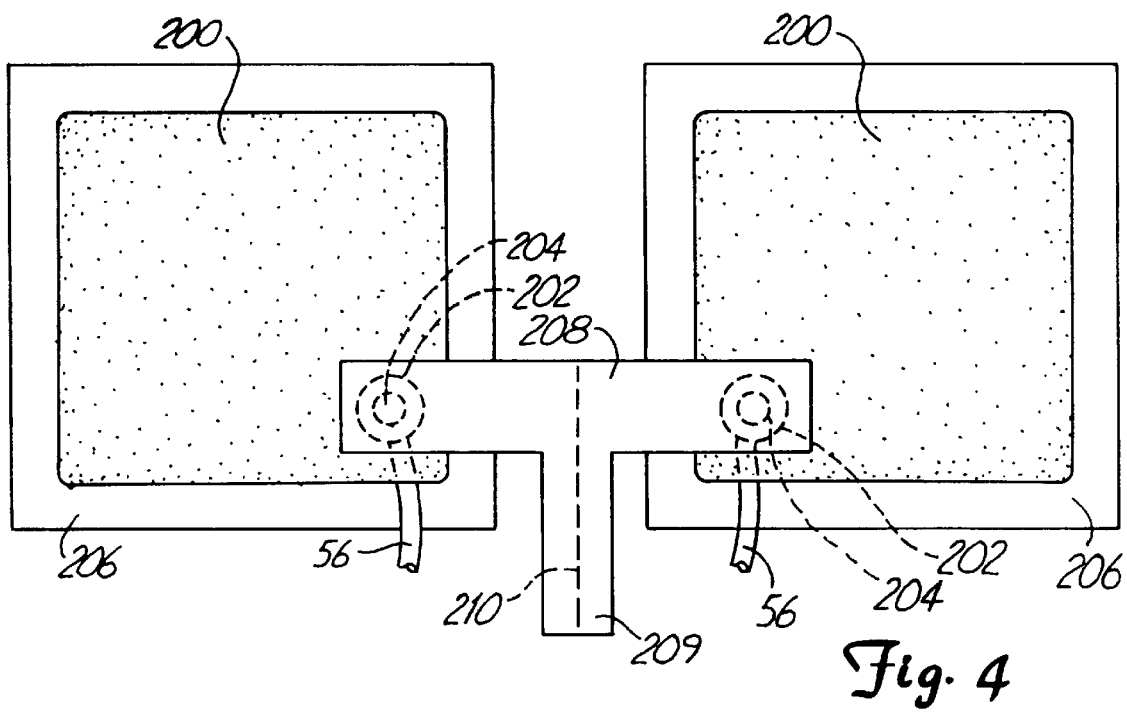
FIG. 4 is detailed plan view of unpackaged electrodes in accordance with a second embodiment of the present invention.

The present invention is a circuit detectable arrangement of medical electrodes and a package therefore. The present invention will be described and illustrated as being connected to an automated external defibrillator (AED) but it should be understood that the present invention is equally applicable to numerous other devices utilizing packaged electrodes.

FIG. 1 illustrates a pair of electrodes 50 connected to an AED 22. As can be seen in FIG. 1, defibrillator 22 includes a plastic case 24 with a carrying handle 26 on the top portion. An illuminable rescue switch 28, visual maintenance indicator 30, data communication port 32 and charging port 34 are located on the outside of case 24 for easy access by an operator. Case 24 also includes an electrode compartment 36 which is enclosed by a lid 38 which is mounted to the case by hinges (not shown). A friction-type releasable latch including pins holds lid 38 closed when defibrillator 22 is not in use. Finger-receiving recess 31 in lid 28 is grasped to open the lid and access the electrode compartment 26. An electrode connector 40, speaker 41 and diagnostic display panel 43 are located on case 24 within electrode compartment 36. The diagnostic display panel includes a visual "Call for Service" indicator light, a "Check Electrode" indicator light, a "Check 9 Volt Battery" indicator light, a "Check 12 Volt Battery" indicator light and a "Power" indicator light.

Defibrillator electrodes 50, as illustrated in FIG. 3, each include a polymer backing layer 52, and a patient-engaging layer 54 of conductive adhesive which overlays the backing layer. In the preferred embodiment of the present invention, backing layer 52 is a flexible polymeric foam. Conductive adhesives for electrode use are well-known and commercially available, such as Ludlou Technical Products' conductive hydrogel. A current-dispersing flexible conductive sheet (not shown) is preferably located between backing layer 52 and patient-engaging layer 54 so as to disperse current over conductive adhesive layer 54. The conductive sheet need not be the same size as the electrode and is preferably a homogeneous, solid, thinly deposited metallic substance, or a conductive ink. Meshes or patterns of conductive adhesives or inks may be used.

Insulated lead wires 56 extend from each electrode 50, and have a first end connected within each electrode 50 to its conductive sheet and a second end connected to a connector 58. Connector 58 is configured to releasably mate with electrode connector 40 in electrode compartment 30, as illustrated. Electrodes 50 are sealed within a polymer or polymer-metal laminate package 60. Lead wires 56 and connector 58 extend from package 60.

A first embodiment of a pair of electrodes 50 to be provided within package 60 is shown in FIGS. 2 and 3. The package design of FIG. 1 illustrates electrodes 50 folded against one another and provided within package 60. As shown in FIG. 2, each electrode 50 includes backing layer 52, patient-engaging layer 54 of conductive adhesive, a conductive sheet 53 (illustrated in FIG. 3) between layers 52 and 54, and a liner 61. Liner 61 can comprise any conventional lining material such as plastic sheeting or treated papers. Both electrodes 50 may be provided together on a single liner sheet; however, for reasons set out below, other compensations would be necessary.

A lead wire 56 connects with each electrode 50. Specifically, lead wire 56 extends partially within each electrode 50, preferably between backing layer 52 and conductive adhesive layer 54. A terminal 62 is provided at the end of lead wire 56 within each electrode 50 for preferably connecting the conductive wire of lead wire 56 to conductive sheet 53. Otherwise, terminal 62 may directly conduct current to conductive adhesive layer 54.

In accordance with the present invention, each terminal 62 preferably extends through backing layer 52 so as to provide a conductor 63 at the surface of backing layer 52. Conductors 63 are connected together electrically by a flexible conductive connector 64. Conductive connector 64 preferably comprises a metal foil or a fine wire which can be folded for packaging and easily torn or broken, the reasons for which will be evident from the description below. Moreover, connector 64 can be conventionally electrically connected to conductors 63 by conductive adhesive, heat bonding solder, or the like. Preferably, conductors 63 and conductive connector 64 are positioned and arranged, such as that illustrated in FIG. 2, so that when electrodes 50 are to be packaged within package 60, they can be folded against one another by a fold line 65 bisecting conductive connector 64. By this arrangement, an electrical circuit can be completed between lead wires 56 through terminals 62, conductors 63, and connecting conductor 64. Also preferably provided, is a strip of tear resistant material 66 that is more preferably provided at about the mid-point of conductor connector 64 and which extends transverse to the direction of connector 64. Tear resistance strip 66 may comprise a plastic, paper or other non-conductive material which is tear resistant as compared to the material of conductive connector 64.

Referring back to FIG. 1, electrodes 50 are folded toward one another along fold line 65 and positioned within a pouch type package 60 that can be conventionally made either of two sheets connected together or a single sheet folded and sealed at its edges 67. One of sealed edges 67 accommodates the passage of lead wires 56 from package 60 by forming a small opening through the edge. Preferably also, edge 67 also accommodates passage of a portion of tear resistant strip 66 from the interior of package 60 to the outside of package 60. A tear line 69 is also provided along package 60 dividing interior portion 68 of package 60 from the rest of the inside of the package that is inhabited by the folded pair of electrodes. Tear line 69 may be facilitated by a line of weakening or other means for controlling package opening along tear line 69. Conductive connector 64 preferably extends within package 60 sufficiently from each electrode 50 into package interior portion 68 so that tear resistant strip also lies completely within interior portion 68.

To open package 60, a user is instructed to tear the package along tear line 69. The portion of tear resistant strip 66 extending from package 60 can be used for grabbing by the user to open the package. Otherwise, the user would simply rip along tear line 69. In tearing open package 60 along tear line 69, conductive connector 64 will be likewise torn or broken. Thus, by opening package 60, the circuit between lead wires 56 of electrodes 50 within package 60 will be broken. The provision of tear resistant strip 66 not only provides an extension for grabbing to begin opening package 60, it also ensures that conductive connector 64 will be broken during a tearing operation. As a result of this construction, the presence of an unbroken conductive connector 64 and the subsequent breaking thereof during usage of electrodes 50 can be automatically detected for determining the presence or absence of fresh electrodes 50.

Figure 5:
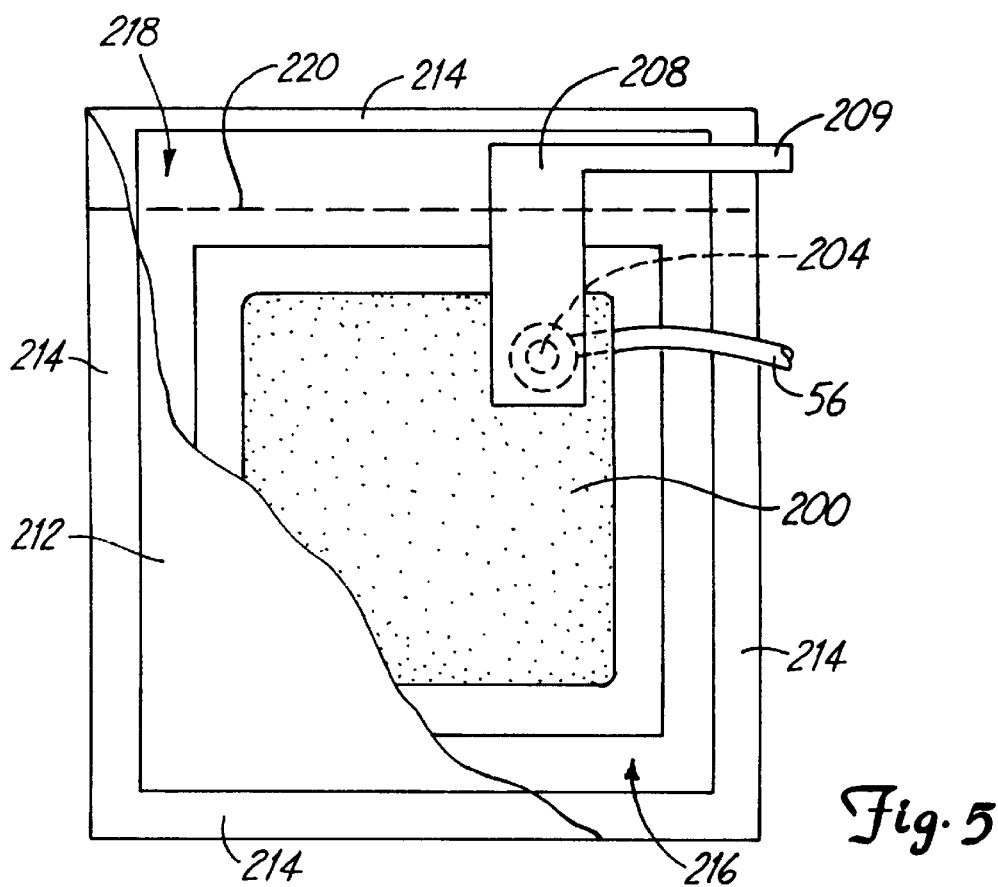
FIG. 5 is a plan view of the electrodes of FIG. 4 folded one on top of the other and provided within a package shown partially broken away.

A second embodiment of a pair of electrodes 200 is illustrated in FIGS. 4 and 5. Specifically, the construction of each electrode 200 is preferably the same as that described above including a backing layer, a patient-engaging conductive adhesive layer, and a current dispersing flexible conducting sheet therebetween. Likewise, lead wires 56 extend partially within electrodes 200 between the backing layer and the conductive adhesive layer of each electrode 200 and are preferably connected with the conductive sheets at terminals 202. Terminals 202 similarly provide conductors 204 at the surface of the backing layers of each electrode 200. Electrodes 200 are each provided on separate liners 206. As with the previous embodiment, a single liner could be used. A pair of electrodes 200 are connected together by a conductive connector 208 specifically connected from one conductor 204 of one electrode 200 to conductor 204 of another electrode 200. Again, conductor 204 can be conventionally connected to conductive connector 208 by conductive adhesive, heat bonding, solder or the like. Conductive connector 208 preferably comprises a thin metal foil. Moreover, in accordance with this embodiment, conductor connector 208 includes an extension portion 209 that is preferably integrally formed with conductive connector 208. Portion 209 extends transversely from conductive connector 208 preferably at about center fold line 210, and extends substantially further than the edge of liners 206.

In order to provide electrodes 200 within a package 212, shown in FIG. 5, the construction and arrangement shown in FIG. 4 is folded substantially on fold line 210 so that electrodes 200 are positioned back to back with liners 206 against one another. Package 212 can be a conventional construction pouch having edge seals 214 around its periphery. Electrodes 200 are received within an electrode interior portion 216 which is divided from an interior portion 218 by a tear line 220. As above, lead wires 56 are accommodated through one of edge seals 214. Likewise, portion 209 of conductive connector 208 preferably extends sufficiently that it extends through the same edge seal to facilitate opening of the package. Conductive connector 208 preferably extends within the package sufficiently from each electrode 200 into package interior portion 218 so that portion 209 of conductive connector 208 lies within in interior package portion 218.

Then, to open package 212, a user would simply grasp the package at or near extension portion 209 and tear the package open along tear line 220. Extension portion 209 ensures that tearing along tear line 220 by grasping extension point 209 will tear through conductive connector 208 and break the circuit between lead wires 56. As above, the function of making and generating the circuit completed by conductive connection 208 and terminals 202 between lead wires 56 can be monitored by defibrillator 22, as described generally below, for determining the presence of fresh electrodes 200.

Figure 6:
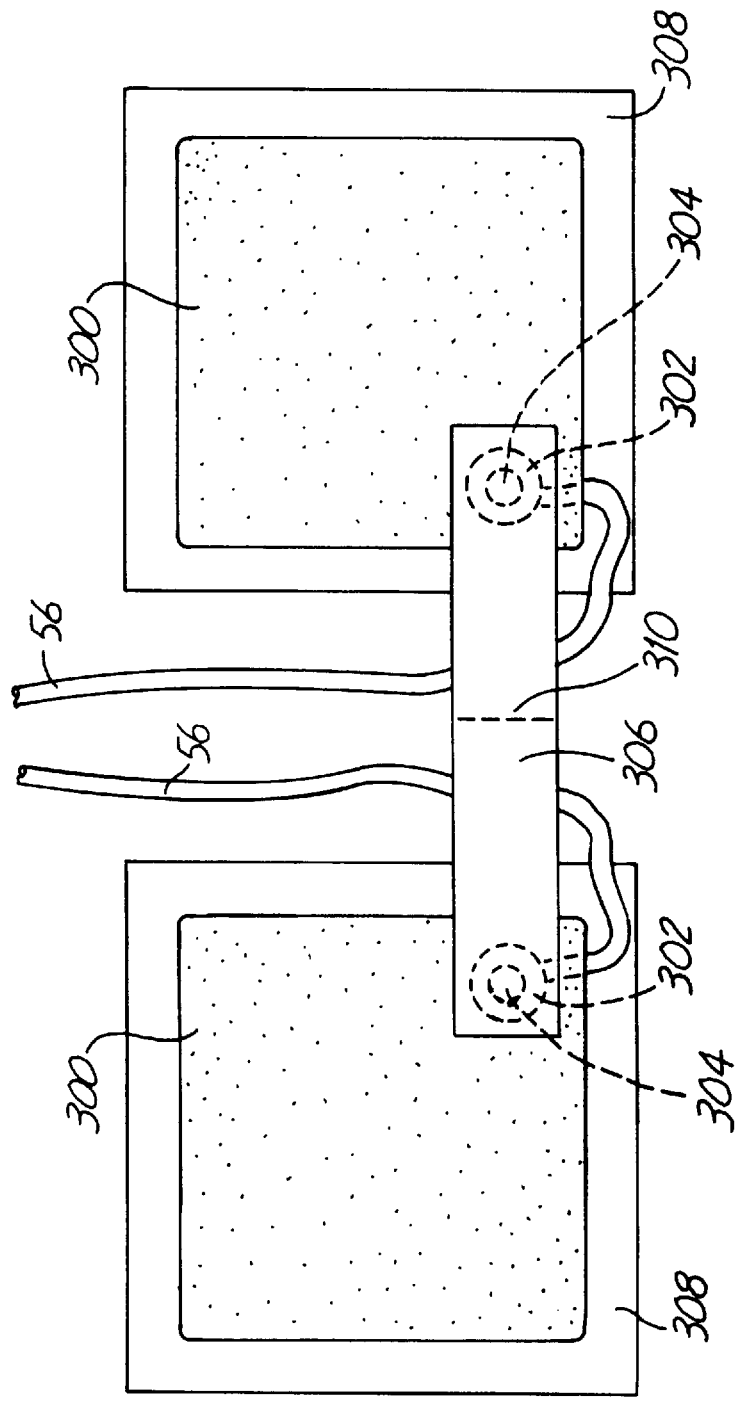
FIG. 6 is a detailed plan view of a pair of unpackaged electrodes in accordance with yet another embodiment of the present invention.
Figure 7:
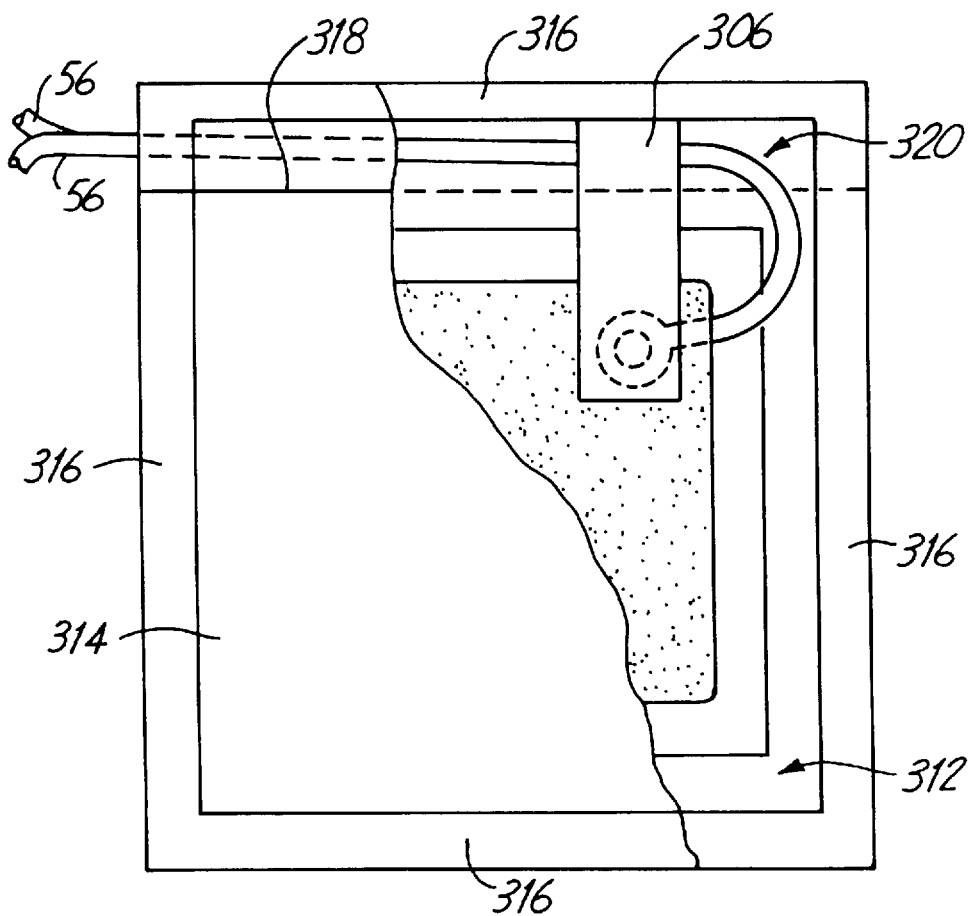
FIG. 7 is a plan view of the electrodes of FIG. 6 folded together and provided within a package shown partially broken away.

Yet another embodiment is illustrated in FIGS. 6 and 7. Electrodes 300 are provided which are similarly constructed as the aforementioned embodiments, including a backing layer, a conductive adhesive layer and a conductive sheet therebetween. Lead wires 56 are preferably connected with the conductive sheets between the backing layer and the conductive adhesive layer by terminals 302. Each terminal 302 also preferably provides a conductor 304 at the surface of the backing layer of each electrode 300. A pair of electrodes 300 are connected together by a conductive connector 306, specifically connected at each end to a conductor 304 of a terminal 302. Again, conventional connection means can be used, such as conductive adhesives, heat bonding, solder or the like. Conductive connector 306 may comprise a thin foil, a fine wire, or the like, but preferably comprises a thin foil. Each electrode 300 is also preferably provided on a separate liner 308. A fold line 310 substantially bisects the conductive connector 306 so that electrodes 300 can be folded back to back with liners 308 against one another. Conductive connector 306 completes an electrical circuit for connecting lead wires 56 by way of terminals 302 and conductors 304.

Electrodes 300 are positioned within an electrode receiving space 312 of package 314 which may be conventionally constructed with sealed edges 316. The interior of the package is divided by a tear line 318 into electrode receiving portion 312 and an interior portion 320.

In accordance with this embodiment, it is important that at least one of lead wires 56 be properly threaded within the package so as to exit package 314 at one of its edge seals 316 from within interior portion 320 of package 314. Moreover, conductive connector 306 forms a loop that extends within interior portion 320 of package 314. Preferably, both of lead wires 56 pass through the loop defined by conductive connector 306 when the electrodes are positioned back to back as folded along fold line 310. More particularly, lead wires 56 pass between conductive connector 306 and an edge of a liner 308. Furthermore, conductive connector 306 is sufficiently long so that when the electrodes are folded back to back, conductive connector 306 forms the loop so as to facilitate both lead wires 56 within interior portion 320. By this embodiment, package 314 can be easily opened along tear line 318 by a user grasping lead wires 56 where they exit package 314 at edge seal 316. Then, tearing the package open along tear line 318 will also tear or break conductive connector 306. Lead wires 56, in this case, act as a tear strip facilitating easy opening of package 314. This construction is advantageous in that in a single action opens the electrode package, breaks the electrical circuit, and removes the electrodes from the package. As above, the function of making and breaking the electrical circuit completed by connector 306 between lead wires 56 can be monitored, as set out below, for determining the presence of fresh electrodes 300.

As an alternative construction to each of the above-described embodiments, liners 61, 206 and 308 could instead comprise a single liner to which both electrodes 50, 200, and 300 respectively, are adhered. To do this, the liners would also be folded to position the electrodes within the respective packages. However, in order to provide that conductive connectors, 64, 208, and 306, respectively, extend across tear lines 69, 220 and 318, respectively, the conductive connectors must be of sufficiently greater length than the distance between the electrodes on the single liner so that when the single liners are folded, the conductive connectors will form a loop that extends sufficiently away from the folded edge of the single liner. It should be noted that the present invention is equally applicable to solid liners and to liners having a plurality of perforations formed therein.

Figure 8:
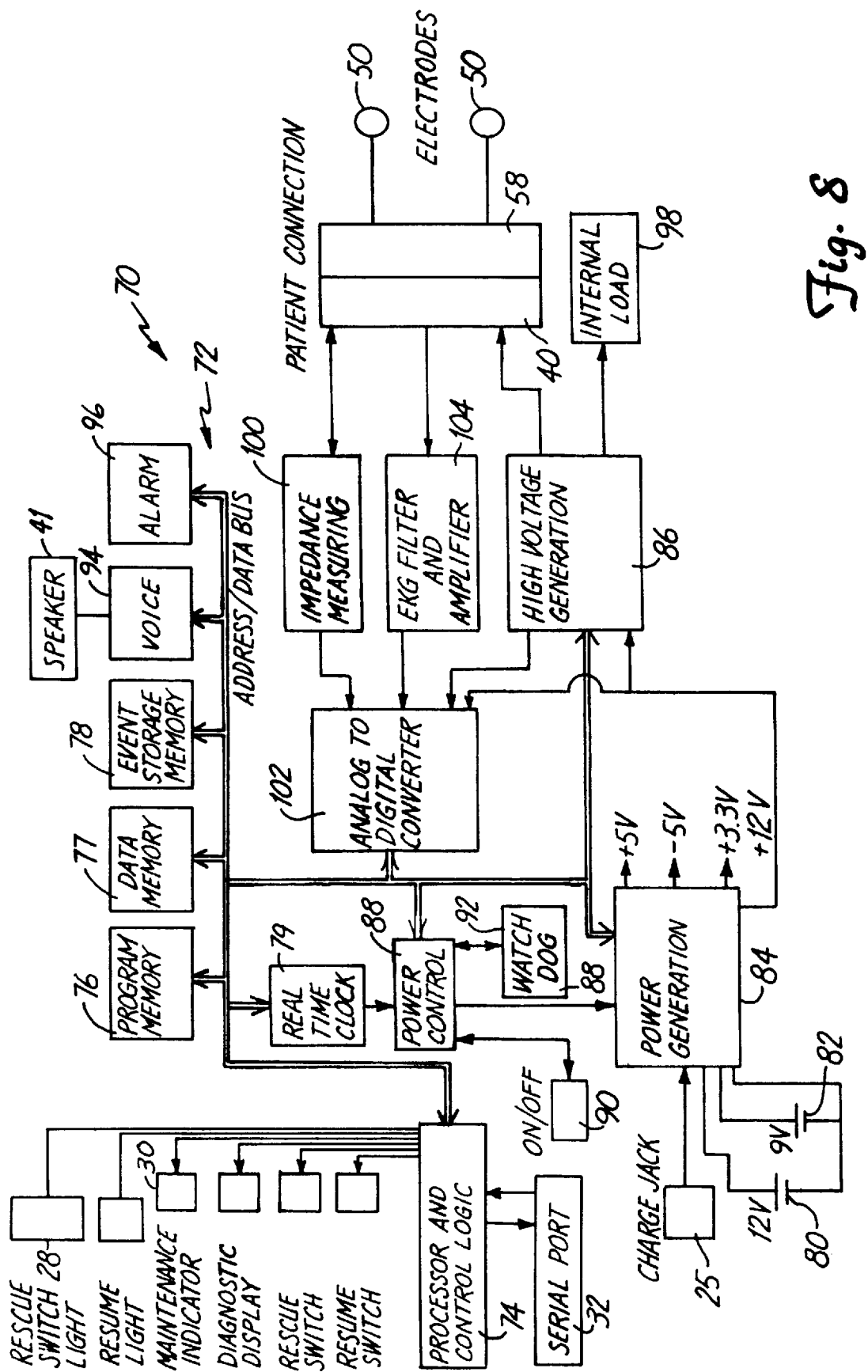
FIG. 8 is a block diagram of an electrical system of an AED.

FIG. 8 is a block diagram of electrical system 70 of defibrillator 10. The overall operation of defibrillator 10 is controlled by a digital microprocessor-based control system 72 which includes a processor 74 interfaced to program memory 76, data memory 77, event memory 78 and real time clock 79. The operating program executed by processor 74 is stored in program memory 76. Electrical power is provided by a rechargeable twelve volt lead-acid cartridge battery 80 and a nine volt battery 82 which are removably positioned within the battery compartment and connected to power generation circuit 84. Charging port 25 is coupled to power generation circuit 84, enabling twelve volt battery 80 to be connected to a twelve volt vehicle battery (not shown) or a 120VAC charger (also not shown) and recharged while mounted within defibrillator 22. Alternatively, battery 80 can be removed from defibrillator 22 and charged in a stand-alone charger (not shown).

Power generation circuit 84 is also connected to power control circuit 88 and processor 74. Power control circuit 88 is connected to lid switch 90, watch dog timer 92, real time clock 79 and processor 74. Lid switch 90 is a magnetic read relay switch in one embodiment, and provides signals to processor 74 indicating whether lid 38 is open or closed. Data communication port 32 is coupled to processor 74 for two-way serial data transfer using an RS-232 protocol. Rescue switch 28, maintenance indicator 30, the rescue switch light, resume switch, indicator lights of the diagnostic display panel, the voice circuit 94 and piezoelectric audible alarm 96 are also connected to processor 74. Voice circuit 94 is connected to speaker 41. In response to voice prompt control signals from processor 74, circuit 94 and speaker 41 generate audible voice prompts.

High voltage generation circuit 86 is also connected to and controlled by processor 74. Circuits such as 86 are generally known, and disclosed, for example, in the commonly assigned Persson et al. U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 40 which is connected to the high voltage generation circuit 86.

Impedance measuring circuit 100 is connected to electrode connector 40 and real time clock 79, and is interfaced to processor 74 through analog-to-digital (A/D) converter 102. Impedance measuring circuit 100 receives a clock signal having a predetermined magnitude from clock 79, and applies the signal to electrodes 50, for example, through connector 40. The magnitude of the clock signal received back from electrodes 50 through connector 40 is monitored by impedance measuring circuit 100. An impedance signal representative of the impedance present across electrode connector 40 is then generated by circuit 100 as a function of the ratio of the magnitudes of the applied and received clock signals (i.e., the attenuation of the applied signal). For example, if electrodes 50 within an unopened package 60 are connected by conductive connector 64 and connector 58 is properly connected to connector 40 on defibrillator 22, a relatively low resistance (e.g., less than about 10 ohms) should be present across connector 40. If package 60 is opened, connector 58 is not properly connected to connector 40, or the electrodes are not properly positioned on the patient, a relatively high resistance (e.g., greater than about two hundred fifty ohms) will be present across connector 40. The resistance across connector 40 will be between about twenty-five and two hundred ohms when fresh electrodes 50 are properly positioned on the patient with good electrical contacts. It should be noted that these resistance values are given as exemplary ranges and are not meant to be absolute ranges. The impedance signal representative of the impedance measured by circuit 100 is digitized by A/D converter 102 and provided to processor 74.

Although the present invention has been described with reference to preferred embodiments, those skilled in the art will recognized that changes can be made in form and detail without departing from the spirit and scope of the invention.

What is claimed is:

1. A plurality of medical electrodes, each electrode comprising an electrically nonconductive backing layer, a patient engaging electrically conductive adhesive layer disposed on said backing layer, said backing layer having a lead wire extending therefrom, the lead wire being in electrical contact with said patient engaging electrically conductive adhesive layer, wherein a first electrode is disposed on a first electrically nonconductive liner, a second electrode is disposed on a second electrically nonconductive liner, and wherein a conductor portion connected between said first and second electrodes adjacent the backing layers for electrically completing a circuit connecting the lead wire of said first electrode to the lead wire of said second electrode.

2. The electrodes of claim 1, wherein said first electrode is provided on a separate liner than the liner of said second electrode.

3. The electrodes of claim 1, wherein the lead wire of each electrode extends partially within the electrode between the backing layer and the conductive adhesive, and a terminal is provided to electrically connect the lead wire within the electrode to the conductive adhesive layer disposed on the backing layer.

4. The electrodes of claim 3, wherein said conductor portion comprises a strip of flexible and electrically conductive material.

5. The electrodes of claim 4, further comprising a nonconductive tear resistant strip connected to said conductor portion.

6. The electrodes of claim 1 wherein the first and second liners have a plurality of holes formed therein.

7. A packaged plurality of medical electrodes, comprising:

a pouch defined by a flexible material and having an interior cavity; and a first medical electrode and a second medical electrode disposed within an electrode receiving space of said interior cavity, each electrode comprising an electrically nonconductive flexible backing layer, a patient engaging electrically conductive adhesive layer disposed on said flexible backing layer, said backing layer having a lead wire extending therefrom, the lead wire being in electrical contact with said patient engaging electrically conductive adhesive layer, wherein said first and second electrodes are each disposed on an electrically nonconductive liner, and wherein a conductor portion is connected between said first and second electrodes adjacent the backing layers for electrically completing a circuit connecting the lead wire of said first electrode to the lead wire of said second electrode.

8. The package of claim 7, wherein the lead wires from said first and second electrodes extend through an opening provided through said package to the outside of said package.

9. The package of claim 8, further including a tear line along which the package is to be opened and which divides the interior cavity of the package into said electrode receiving space and an interior portion.

10. The package of claim 9, wherein said conductor portion comprises a flexible conductive strip, and said first and second electrodes are provided adjacent to one another in said package with their backing layers generally parallel to one another and with a loop formed in the conductor portion, said loop extending across said tear line and into said interior portion of said package from said electrodes within said electrode receiving space so that by opening the package along said tear line, the conductor portion can be broken.

11. The package of claim 10, further including a strip of tear resistant material connected to said conductor portion and positioned within said interior portion.

12. The package of claim 11, wherein said strip of tear resistant material extends through an opening of said package to provide a gripping means to facilitate easy opening of said package.

13. The package of claim 10, wherein said flexible conductive strip includes a portion extending transverse from said loop and which extends through an opening of said package to provide a gripping means to facilitate easy opening of said package.

14. The package of claim 10, wherein at least one of said lead wires is threaded within said package through said loop and within said interior portion so as to pass through the material of said package from said interior portion.

15. The package of claim 10, wherein said first electrode is provided on a separate liner than the liner of said second electrode.

16. The package of claim 10, wherein the lead wire of each electrode extends partially within the electrode between the backing layer and the conductive adhesive, and a terminal is provided to electrically connect the lead wire within the electrode to the conductive adhesive layer disposed on the backing layer.

17. The package of claim 7 wherein the liners of the first and second electrodes have a plurality of holes formed therein.

18. An automated external defibrillator (AED) including a packaged pair of electrodes, wherein the AED has a case, electrode terminals, a battery compartment and battery terminals in the case, a high voltage circuit coupled to the battery terminals and a control system, the packaged pair of electrodes comprising:

a package comprised of flexible material defining a pouch having an interior cavity;

first and second electrodes within an electrode receiving space of said interior cavity wherein each electrode includes an electrically nonconductive flexible backing layer and a patient engaging electrically conductive adhesive layer disposed on said flexible backing layer, said flexible backing layer having a lead wire extending therefrom, the lead wire being in electrical contact with said patient engaging electrically conductive adhesive layer, wherein said first and second electrodes are each disposed on an electrically nonconductive liner; and a conductor portion connected between the first and second electrodes and adjacent the backing layers for connecting the first and second electrodes, thereby electrically completing a circuit connecting the lead wire of said first electrode to the lead wire of said second electrode.

19. The AED of claim 18, wherein the lead wires from said first and second electrodes extend through an opening provided through said package to the outside of said package.

20. The AED of claim 18, further including a tear line along which the package is to be opened and which divides the interior cavity of the package into said electrode receiving space and an interior portion.

21. The AED of claim 20, wherein said conductor portion comprises a flexible conductive strip, and said first and second electrodes are provided with their backing layers generally parallel to one another and with a loop formed in the conductor portion, said loop extending across said tear line and into said interior portion of said package from said electrodes within said electrode receiving space so that by opening the package along said tear line, the conductor portion can be broken.

22. The AED of claim 21, further including a strip of tear resistant material connected to said conductor portion and positioned within said interior portion.

23. The AED of claim 22, wherein said strip of tear resistant material extends through an opening of said package to provide a gripping means to facilitate easy opening of said package.

24. The AED of claim 21, wherein said flexible conductive strip includes a portion extending transverse from said loop and which extends through an opening of said package to provide a gripping means to facilitate easy opening of said package.

25. The AED of claim 21, wherein at least one of said lead wires is threaded within said package through said loop and within said interior portion so as to pass through the material of said package from said interior portion.

26. The AED of claim 21, wherein said first electrode is provided on a separate liner than the liner of said second electrode.

27. The AED of claim 21, wherein the lead wire of each electrode extends partially within the electrode between the backing layer and the conductive adhesive, and a terminal is provided to electrically connect the lead wire within the electrode to the conductive adhesive layer disposed on the backing layer.

28. The AED of claim 18 wherein the liners of the first and second electrodes have a plurality of holes formed therein.

* * * * *